(12) United States Patent
Fichtler et al.

(10) Patent No.: US 11,896,376 B2
(45) Date of Patent: Feb. 13, 2024

(54) AUTOMATED IMPAIRMENT DETECTION SYSTEM AND METHOD

(71) Applicant: Gaize, Missoula, MT (US)

(72) Inventors: Kenneth Hunter Fichtler, Missoula, MT (US); Robert Nelson Lass, Havre, MT (US)

(73) Assignee: Gaize, Missoula, MT (US)

( * ) Notice: Subject to any disclaimer, the term of this patent is extended or adjusted under 35 U.S.C. 154(b) by 0 days.

(21) Appl. No.: 18/100,103

(22) Filed: Jan. 23, 2023

(65) Prior Publication Data

US 2023/0233120 A1 Jul. 27, 2023

Related U.S. Application Data

(60) Provisional application No. 63/303,604, filed on Jan. 27, 2022.

(51) Int. Cl.
| | |
|---|---|
| *A61B 5/16* | (2006.01) |
| *A61B 5/145* | (2006.01) |
| *A61B 5/00* | (2006.01) |

(52) U.S. Cl.
CPC .......... *A61B 5/163* (2017.08); *A61B 5/14517* (2013.01); *A61B 5/4266* (2013.01); *A61B 5/4845* (2013.01); *A61B 5/7264* (2013.01)

(58) Field of Classification Search
CPC ... A61B 5/163; A61B 5/14517; A61B 5/4266; A61B 5/4845; A61B 5/7264
See application file for complete search history.

(56) References Cited

U.S. PATENT DOCUMENTS

| | | | | |
|---|---|---|---|---|
| 6,139,152 | A * | 10/2000 | Ghahramani | ........ H04N 13/327 351/243 |
| 7,027,621 | B1 | 4/2006 | Prokoski | |
| 7,127,376 | B2 * | 10/2006 | Nashner | ................. A61B 5/486 702/185 |
| 7,357,507 | B2 | 4/2008 | Waldorf et al. | |
| 7,388,166 | B2 | 6/2008 | Marmaropoulos et al. | |
| 7,614,745 | B2 | 11/2009 | Waldorf et al. | |
| 8,111,283 | B2 | 2/2012 | Kim et al. | |
| 8,226,574 | B2 * | 7/2012 | Whillock | ............. A61B 5/4863 351/210 |
| 8,878,669 | B2 | 11/2014 | Nothacker et al. | |
| 8,899,748 | B1 | 12/2014 | Migdal | |

(Continued)

*Primary Examiner* — Jonathan T Kuo
(74) *Attorney, Agent, or Firm* — Parsons Behle & Latimer

(57) ABSTRACT

Systems and methods to determine if an individual is impaired. The system includes a display and a stimulus on the display. The system include a controller that is programmed to move the stimulus about the display and one or more sensors that track eye movements and pupil size of a user due to movement of the stimulus or light conditions. The system includes a processor programmed to analyze the eye movements and pupil data size. The method includes using a testing apparatus and collecting data from the testing apparatus. The method includes storing the collected data. The method includes processing the data with an automated impairment decision engine to determine whether a test subject is impaired. The method may include using machine learning models or statistical analysis to determine whether a test subject is impaired. The automated impairment decision engine may be trained using machine learning and/or statistical analysis.

27 Claims, 3 Drawing Sheets

(56) References Cited

U.S. PATENT DOCUMENTS

| | | | |
|---|---|---|---|
| 8,911,085 B2 | 12/2014 | Privitera et al. | |
| 9,788,714 B2 | 10/2017 | Krueger | |
| 9,888,845 B2 | 2/2018 | Visconti | |
| 9,994,228 B2 | 6/2018 | Krueger | |
| 10,070,787 B2 | 9/2018 | Visconti | |
| 10,376,183 B2 | 8/2019 | Macknik et al. | |
| 10,575,726 B2 * | 3/2020 | Wetzel | A61B 5/1103 |
| 10,653,358 B2 | 5/2020 | Nothacker et al. | |
| 11,154,203 B2 * | 10/2021 | Frank | G01J 3/0264 |
| 11,490,809 B2 * | 11/2022 | Krueger | G06F 3/012 |
| 2005/0075833 A1 * | 4/2005 | Nashner | A61B 5/1036 |
| | | | 702/179 |
| 2009/0115966 A1 | 5/2009 | Waldorf et al. | |
| 2010/0016754 A1 * | 1/2010 | Whillock | G16H 50/20 |
| | | | 600/558 |
| 2015/0379362 A1 | 12/2015 | Calmes et al. | |
| 2016/0022137 A1 * | 1/2016 | Wetzel | A61B 5/4076 |
| | | | 600/558 |
| 2019/0191995 A1 * | 6/2019 | Giovinazzo | A61B 3/113 |
| 2020/0022622 A1 | 1/2020 | Macknik et al. | |
| 2020/0121195 A1 * | 4/2020 | Bresler | A61B 3/112 |
| 2020/0305708 A1 * | 10/2020 | Krueger | G06F 3/013 |
| 2020/0397306 A1 * | 12/2020 | Frank | G01J 5/10 |
| 2021/0150757 A1 * | 5/2021 | Mustikovela | G06N 3/08 |
| 2022/0073079 A1 * | 3/2022 | Nilsson | B60K 28/063 |
| 2022/0386953 A1 * | 12/2022 | Mohammadian Roshan | |
| | | | G06T 7/292 |

* cited by examiner

AUTOMATED IMPAIRMENT DETECTION SYSTEM AND METHOD

RELATED APPLICATION

This application claims the benefit of priority under 35 U.S.C. § 119 to U.S. Provisional Patent Application Ser. No. 63/303,604 entitled "AUTOMATED IMPAIRMENT DETECTION SYSTEM AND METHOD" filed on Jan. 27, 2022, which is incorporated herein in its entirety.

FIELD OF THE DISCLOSURE

This disclosure is generally related to an automated way to detect active (real-time) impairment from cannabis and other drugs, or abnormal mental conditions like fatigue through the utilization of gaze vector data, pupil size data, and optionally other biometric data, evaluated by machine learning algorithms and optionally other statistical methods.

BACKGROUND

There is presently no automated system which can quickly and accurately determine active impairment from a broad variety of drugs, legal and illicit, including alcohol, cannabis, central nervous system depressants, central nervous system stimulants, opiates, and more. Further, there is an acute need to detect and quantify mental states like fatigue as a way to facilitate safe driving and working conditions. Cannabis and other drugs are being rapidly legalized in the United States. This has created the problem of an increased need to understand cannabis and other drug impairment due to increased utilization. In states where cannabis or other drugs are legal and because the compounds linger in a user's body, it is now insufficient to determine the simple presence in the body of impairing molecules (like delta-9-tetrahydrocannabinol, or tetrahydrocannabinol (THC), in cannabis) to determine if a crime, like driving under the influence (DUI), has been committed.

In order to allow for rapid field identification of active impairment on a variety of substances, the human conducted Standardized Field Sobriety Tests (SFST) are commonly used. Originally researched and developed from 1975 to 1981 by the National Highway Traffic and Safety Administration (NHTSA), the Standardized Field Sobriety Tests are intended to allow a police officer with no tools other than their observations to determine if a subject is impaired. These tests have been repeatedly validated as reliable measurements of impairment in alcohol, cannabis, and some other drugs. They are based on the scientific understanding of how alcohol, cannabis and other drugs impact a user's ability to conduct basic tests of balance and dexterity, and most importantly, how these substances impact involuntary eye movement. When properly administered, the Standardized Field Sobriety Tests give officers "probable cause" to arrest a vehicle operator for driving under the influence or driving while impaired. The Drug Recognition Expert (DRE) program expands on the SFSTs for a total of 12 testing steps. DRE officers are the best trained law enforcement officers at determining drug impairment. They go to a special school where they learn to perform these tests and interpret the results. Drug Recognition Experts are the only mechanism currently available that can detect active cannabis impairment, as well as active impairment from drugs other than alcohol.

Although the SFST and Drug Recognition Expert battery tests have been proven accurate at establishing whether or not a vehicle operator is under the influence of an intoxicating substance, Drug Recognition Expert officers and other officers who conduct field sobriety tests are subject to inescapable opportunities for inaccuracy. Those include: human error in conducting or interpreting tests, subjectivity of interpretation in test results, errors due to adverse testing conditions, and a distinct lack of corroborating evidence generated in the process to validate an officer's determination. This leads to the results of the tests being routinely called into question by defense attorneys during the course of a DUI trial.

Despite intensive and challenging training, the opportunity for human error is omnipresent due to the precision that properly conducting the tests requires and the reliance on memorized test procedures. In particular, the tests that deal with eye movement are multi-part and rely on providing a stimulus of appropriate distinction, size, distance, speed, and angle from the subject's eyes. It is therefore exceedingly difficult to conduct the tests in a precisely standardized fashion every time they are administered, and even more difficult to simultaneously accurately interpret the resulting eye movement behavior. To allow human error in a process with such important and impactful ramifications is unacceptable.

Compounding these challenges is the distinct lack of objective data generated in the process. The only current output of the test is simply the notes taken by the administering officer, and perhaps a body-camera or dash-camera video recording, if they were activated. Unfortunately, these videos are not commonly of sufficient quality or steadiness to observe eye movement, which is a fundamental component of the Standardized Field Sobriety Tests and Drug Recognition Expert evaluation. Other drawbacks and issues also exist.

In view of the foregoing, a need exists for an improved impairment identification system and method for police officers in an effort to overcome the aforementioned obstacles and deficiencies of conventional human-conducted impairment testing systems.

SUMMARY

One embodiment of the present disclosure is a system. The system includes a display and a stimulus on the display. The system include a controller that is programmed to move the stimulus about the display. The controller may be programmed to control light conditions for the user. The system includes one or more sensors that track eye movements and pupil size of a user due to movement of the stimulus or light conditions. The system includes a processor programmed to analyze the eye movements and pupil data size.

The controller may be programmed to move the stimulus to perform an impairment test and the processor may be programmed to determine and evaluate impairment based on data from the one or more sensors. The controller may be programmed to stimulate pupil response using varying light conditions to perform an impairment test and the processor may be programmed to determine and evaluate impairment based on data from the one or more sensors. The one or more sensors may capture pupil size data and the processor may be programmed to analyze the pupil size data to evaluate impairment.

The one or more sensors may capture gaze vector data of the user's vision and the processor may be programmed to analyze the captured gaze vector data to evaluate impairment. The display may be a virtual reality headset, television, monitor, kiosk-mounted display, augmented reality glasses, a holographic display, or the like. The processor may be programmed to utilize statistical models, machine learning, artificial intelligence algorithms, or a combination of these to analyze the eye movements or other biometric data. The controller may be programmed to precisely calibrate the system to a face shape, eye characteristics, and eye geometry of the user. The controller may be programmed to move the stimulus smoothly to the left and right, up and down, or in any other motion.

The controller may be programmed to move the stimulus one or more times to a horizontal periphery of the user's vision. The controller may be programmed to move the stimulus left or right and stop the movement at 45 degrees from center. The controller may be programmed to move the stimulus to a vertical periphery of the user's vision. The controller may be programmed to move the stimulus in a circle or to stimulate convergence in focus by bringing the stimulus toward the subject's nose. The controller may be programmed to display specific light levels and measure pupillary reflex response. The controller may be programmed to capture data using skin-contact or non-contact sensors, such as temperature, heart rate, heart rate variability, respiratory rate, pulse oxygenation, heart rhythm, blood pressure, and muscle tone. The controller may be programmed to perform chemical analysis on the sweat excreted by the test subject. The controller may be programmed to measure lack of convergence, saccades, nystagmus, hippus, eye smoothness, reaction time, pupillary rebound dilation, and pupillary reflex for the purposes of impairment detection.

One embodiment of the disclosure is a method of using a testing apparatus and collecting data from the testing apparatus. The method includes storing the collected data. The method includes processing the data with an automated impairment decision engine to determine whether a test subject is impaired. The method may include using machine learning models or statistical analysis to determine whether a test subject is impaired.

One embodiment of the disclosure is a method of capturing data from participants in both an impaired state and an unimpaired state. The method includes applying captured data to unsupervised machine learning. The method includes applying captured data to supervised machine learning. The method includes applying captured data to statistical analysis. The method includes implementing the results of the unsupervised machine learning, supervised machine learning, and statistical analysis to create an automated impairment decision engine to determine whether a test subject is impaired or unimpaired.

Figure 1:
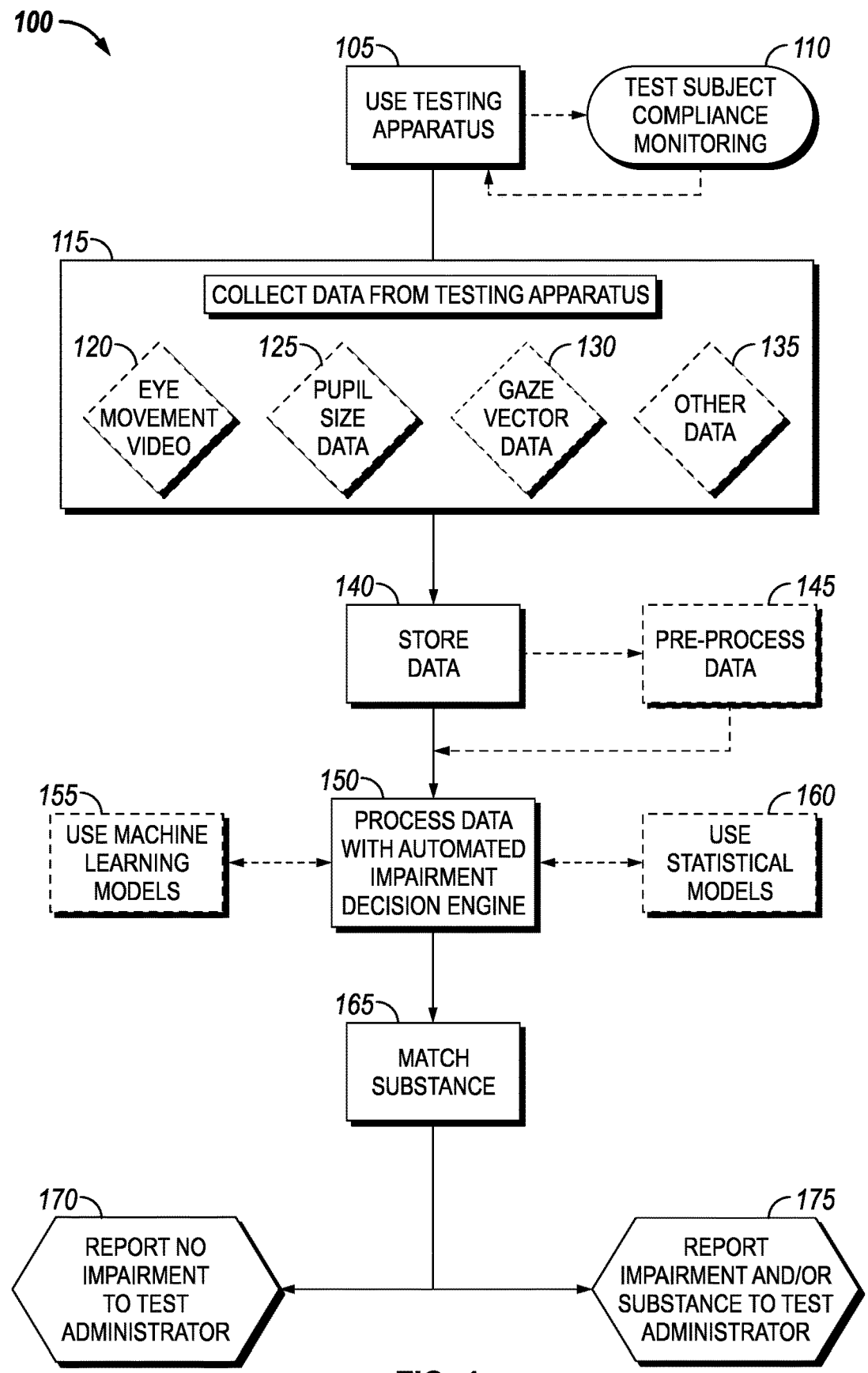
FIG. 1 is a flow chart of an embodiment of a method of the present disclosure.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

The disclosure includes systems and methods that radically improve upon the shortcomings of human conducted Standardized Field Sobriety Testing and Drug Recognition Expert testing methods through the use of unique technology that acts upon the same and new indicators of impairment in the human body as do these human-performed tests. In an embodiment, the system is functionally an automated way to detect active (real-time) impairment from cannabis and other drugs, fatigue, or other conditions through the utilization of gaze vector data, pupil size data, and optionally other biometric data, evaluated by machine learning algorithms and/or statistical methods. By measuring the physiological signs and symptoms of impairment through a device that runs fully automated tests, a significant improvement in identification of active single or poly-drug impairment, fatigue, or other conditions is achieved. These tests include those designed to elicit eye movement, measurement of pupil size and rate of dilation, measurement of pulse rate, evaluation of blink characteristics, quantification of body sweat volume or composition, measurement of body temperature, blood oxygenation, heart rate, heart rate variability, heart rhythm, blood pressure, respiratory rate, pulse oxygenation, muscle tone and other biometric characteristics which may be correlated with impairment or sobriety.

An embodiment of the system uses a head-mounted apparatus or a fixture-mounted apparatus with a digital screen or projection on which a stimulus and/or varying levels of light conditions can be displayed, such as a virtual reality headset or an augmented reality headset. This stimulus shall be tracked by the test subject's eyes in order to perform the tests. The apparatus further includes one or more eye tracking sensors or cameras, and optionally, other biometric sensors for the purpose of capturing biometric data as discussed above. Those sensors may include pulse sensors, moisture sensors, pupil size sensors, temperature sensors, or other biometric data capture sensors such as skin-contact sensors.

The apparatus is designed for the test subject to place their face on or near while the test is conducted. A fixture-mounted apparatus may be most useful in situations in which a high rate of test subject throughput can be expected. Rather than being affixed to the test subject's head, the fixture mounted variant requires test subjects to place their head in a particular location or position so the apparatus may conduct the tests of eye movement, and so the other optional sensors may capture data.

The tests are conducted by controlling the light levels that enter the eyes, and/or displaying a stimulus (typically a colored dot or ball or the like) on the apparatus' digital screen. The stimulus is automatically moved according to the programmed testing parameters, or other dynamically adjusted testing parameters, and the test subject is instructed to follow the stimulus with their eyes. The system may include a controller, or the like, may be used to move the stimulus about the digital screen in various patterns and/or directions as discussed herein. Through the use of eye tracking sensors and/or cameras in the apparatus, the system tracks and captures the test subject's eye movement video and/or still imagery, eye gaze vector data, pupil size measurements, and may collect other biometric data as the test runs automatically. The eye video, eye positional coordinates, gaze vectors, and pupil size of the eyes are precisely computed and stored for evaluation by the system. Storage of the resulting data may occur locally, on removable or non-removable media, or on a cloud server, or other remote storage location. Other optional biometric data such as, but not limited to, temperature, moisture, and pulse sensors can also be captured and stored for evaluation of the test subject.

The evaluative statistical and/or machine learning/artificial intelligence algorithms are trained using a dataset of impaired and sober individuals whose impairment characteristics are known. This produces algorithms that detect eye movement and pupil size characteristics that can be correlated with precise levels of impairment. Utilizing this technique, an extremely high degree of accuracy in determining sobriety, impairment, or a variety of other medical conditions can thus be obtained. This machine learning algorithm may be trained to act more quickly and with greater accuracy and objectivity than any human. The use of this automated testing technology represents a significant advance in the detection of impairment from one or multiple substances, fatigue, and other conditions.

In order to ensure testing accuracy, the frame rates of the apparatus' digital display, the eye tracking sensors and other biometric sensors may be synced. By eliminating small variations between frame rates or data capture rates on eye tracking sensors, cameras, and other biometric sensors, the most precise measurements are obtained. The statistical, machine learning/artificial intelligence algorithms can also be trained to compensate for variability in sensor data capture rates.

Upon use of the testing apparatus, the system may use any collected data, such as, but not limited to eye tracking, pupil size, corneal, eye measurements, or the like, to automatically identify the test subject. This may be useful in cases where repeated testing or regular testing is required (for example, construction sites or other workplaces). Examples of data which may be utilized to automatically identify a test subject includes eye measurement data such as interpupillary distance, or any other data captured by the system, such as eye movement characteristics, corneal print, image recognition, pupil size, or other biometric data. The system may utilize this test data to automatically match the test subject against a database of known test subjects. This test subject matching algorithm can then be utilized to group a test subject's test data together, to send test results to specific third parties, or to allow the system to administer certain tests which may be most relevant to that user.

The test subject matching algorithm can be trained by the system by conducting one or multiple tests which capture the required biometric data. This data is then characterized and stored in a database. When a test subject begins a test, their biometric data can then be accessed and the test subject matched against the database. Test subjects may be added or removed by a test administrator or other third party. If a test subject is found to not be in the database, a test may still be conducted, and the results sent to any third party as required.

While the test apparatus conducts the automatically performed tests, the apparatus collects gaze vector data, pupil size measurement data, and other optional biometric data. This data is then automatically evaluated by a processor, or the like, programmed to use statistical models, and/or machine learning or artificial intelligence algorithms to identify characteristics within the data that are consistent with impairment and/or sobriety. The data processing may take place on the testing apparatus, on another electronic device such as a mobile phone or tablet or using remote cloud computing infrastructure. Some or all tests may be dynamically modified by the system if required. For example, the system may compute the periphery of vision for a user and move the stimulus to that computed periphery. The results may be presented on the apparatus, sent to a third party (like the test administrator) using any electronic means, or displayed on a mobile application.

Tests that may be automatically performed by the apparatus may include the following, as well as other tests which seek to elicit eye movement which can be correlated with impairment.

Calibration—This test seeks to precisely calibrate the system to the face shape, eye characteristics and eye geometry of the user. The eye movement of the user is measured during a multi-part test that may include measuring interpupillary distance, eye tracking using a moving or stationary stimulus, the measurement of pupil size, blink rate, and other biometric or eye movement characteristics. Utilizing this data, the system may make adjustments to the software or hardware of the testing apparatus to precisely align the eye tracking sensors, eye cameras, and other biometric sensors to capture optimal data. The calibration test may additionally measure reaction time, and capture eye movement data during the calibration test for later evaluation by the machine learning/artificial intelligence algorithm. In some cases, a user's facial geometry may fall outside of the parameters that are testable by the apparatus. In these cases, the system may notify the user and/or the test administrator or other interested parties.

Lack of Smooth Pursuit—This test evaluates a user's ability to track a stimulus smoothly with the eyes only. The system conducts this test by moving the stimulus smoothly to left and right, and/or up and down one or more times. An impaired person's eyes may exhibit saccades, or jerking, in the motion of their eyes.

Horizontal Gaze Nystagmus—tests for involuntary jerking movement of the eyes at the left and right periphery of vision. The system conducts this test by moving the stimulus to the left and/or right periphery of the user's vision one or more times. An impaired person's eyes may exhibit nystagmus, or sustained jerking motion, in the eyes during stationary focus.

Onset of Horizontal Gaze Nystagmus Before 45 Degrees—tests for involuntary jerking of the eye using a stimulus held at 45 degrees or less horizontally from center. Similar to the Horizontal Gaze Nystagmus test above, the system moves the stimulus left and/or right one or more times. However, this test stops the stimulus at or before 45 degrees from center. The test may also stop the stimulus as soon as nystagmus is detected and record the angle of onset. An impaired person's eyes may exhibit nystagmus at angles of onset that are not on the periphery of vision.

Vertical Gaze Nystagmus—tests for involuntary jerking of the eye at the upper or lower periphery of vision. The system conducts this test by moving the stimulus up and/or down to the upper and/or lower periphery of the user's vision one or more times. The system may also stop the stimulus as soon as nystagmus is detected and record the angle of onset. An impaired person's eyes may exhibit nystagmus on the upper or lower peripheries of vision, or at an angle of onset prior to the periphery.

Lack of Convergence—tests for the ability to converge the eyes and/or hold them in that position. The system moves a stimulus in a circle, which may be 12" in diameter, or another size, then moves the stimulus slowly toward the bridge of the nose. The stimulus may stop approximately 2" from the bridge of the nose, or another distance. The system may also move the stimulus directly toward the bridge of the nose, omitting the aforementioned circle, and may repeat this test one or more times. This test should cause a user's eyes to cross (converge in focus). An impaired person's eyes may exhibit a lack of ability to converge the focus of the eyes (lack of convergence) or a lack of ability to hold the eyes in a converged position, or other abnormal characteristics.

Pupillary Rebound Dilation—tests the involuntary pupil reflex response to changing light conditions. The system may optionally remove the stimulus or replace it with another focus, such as a timer. The system may display a variety of light levels, including but not limited to room light, full dark, and bright light. In the room light condition, the system may simulate the amount of light in a normally lit room. In the full dark light condition, the system may remove all or most ambient light from the display. This "blacked out" state persists until the user's eyes are fully dilated in response—this may be 90 seconds, or another period of time. The system may then increase the light level to bright light to test how the pupils respond to light. The system may change light levels for both eyes simultaneously or individually. The system measures pupil size throughout this test and may optionally monitor eye movement. The rate at which a user's pupil responds to a change in light conditions may indicate impairment. For example, a person's pupils may persist in a dilated or constricted state, depending on the substance a person is impaired on. Further, the pupils may display pupillary unrest or hippus, in which the pupils may not stop adjusting size, despite steady light conditions. This presents as a constricting and dilation of the pupils, and it may be either significant or very subtle.

Reaction Speed—this test seeks to quantify a user's reaction time as a reduction or increase in reaction time is indicative of impairment on certain substances. This test may be derived from reaction times in response to changes in the previously mentioned tests, or it may be performed through the appearance or movement of a stimulus in a randomly generated quadrant of the testing apparatus display. The system generates a location at which to display the stimulus using a random number generator. Each number is assigned to a location on which the system may display the stimulus. Once the random number generator has determined a location for the stimulus, the system displays the stimulus and measures the time required for the user's eyes to land on the stimulus. The test may use a stimulus that moves to the next location or disappears and reappears in the next location. The test may be repeated multiple times to determine a representative reaction time for the user.

All of the tests detailed above may be conducted with the stimulus positioned as needed, though a virtualized distance of 12"-15" from the user's eyes, unless otherwise noted, has been utilized thus far. The size of the stimulus can be variable or fixed as required. The head should not move during these tests, and the testing apparatus may detect such movement and provide user and/or administrator with appropriate feedback, as well as automatically pause, or restart the tests as required.

The system may additionally utilize programmatic, statistical or machine learning/artificial intelligence methods to determine if a user is following test instructions during the testing process. A non-compliant user may, for example, simply close one or both of their eyes for some or all of the testing process. Other types of non-compliance can include, but are not limited to, looking straight ahead or at another random point for the duration or part of the testing process, moving the eyes in a random manner for some or all of the testing process, tracking the stimulus only intermittently, ignoring test instructions, rapidly blinking for a sustained period of time, or cessation of stimulus tracking at any point. The detection of non-compliant users and the subsequent notification of non-compliance to test administrators or other interested parties is an important step in accurately determining impairment.

When complete, the tests may be uploaded to a cloud server for processing or processed on the device or a mobile application. The resulting test data may be compressed prior to transmitting to any other device using either lossless, or lossy compression methods. Known compression methods may be utilized in this step.

Either supervised or unsupervised machine learning techniques may be used to create accurate impairment detection models. Initial data processing may include data normalization and cleaning. This will simplify and format the data to eliminate unnecessary timesteps, simplify 3-dimensional rotations, and split each resulting series of data into logical components according to the targeted movement patterns. A time-series statistical model may be utilized to determine initial fit of the data against known characteristics of impairment. This may be followed by deep learning evaluative techniques. Specifically, clustering with Fourier Transforms, and ROCKET algorithms may be utilized to establish a baseline. These algorithms both automate the process of feature engineering, and they provide complimentary visual interpretations. This baseline can then be measured against two architectures: Dilated Convolutional Neural Networks, and Deep Learning based attention models.

Time Series Analysis—Baseline Clustering Fourier Transform: For data with a periodic nature, the entire dataset may be described by a linear combination of wave functions, allowing the definition of its location in a new coordinate system. Having the recordings mapped in this new system can allow them to be compared, clustered, and visualized spatially. Algorithms such as k-nearest neighbors, basic multi-layer perceptrons, convolutional neural networks, random forest classifier based on catch22 features, Diverse Representation Canonical Interval Forest Classifier, TSFresh classifier, or WEASEL may be applied to classify this time series data into behaviors and impairment levels.

Time Series Analysis—Classification with ROCKET Algorithm: Rather than using different waves as features, ROCKET uses a set of wavelets, finite segments of waves. The ROCKET algorithm starts by generating approximately 10,000 wavelets of random shapes, sizes, and dilations. The weight of each wavelet feature in a recording is how prevalent the pattern of that wavelet is along the recording. If the pattern shows up many times in the recording, the value for that feature will be higher than if the pattern appears seldom or not at all. This may be used to further classify characteristics of impairment and sobriety. In the ROCKET algorithm these features are then used as the variables in a linear classifier, such as ridge regression classification.

Deep Learning Analysis—Classification with Dilated Convolutional Neural Network: Deep learning methods have higher performance (and better generalization) than classifying with the two previously discussed baselines. A deep learning model called WaveNet using convolutional neural network architecture that uses dilated convolution layers to scale to larger sequences in a memory-efficient way may be utilized. While typically used for forecasting, it can be adapted for classification. Like the kernel size of a typical convolutional layer, the dilation size in the dilated convolutional layers can be adjusted to fit the needs of the data. In this case, the dilation size may be set such that the kernel of the outermost layer covers a full target movement and tracking event.

Deep Learning Analysis—Classification with Transformers—Deep Learning: Transformers may be applied to a sequence of eye movements in much the same way that transformers are applied to sequences of words in natural language processing. Like the other approaches, this algorithm finds a set of common features to describe eye movements and transforms each into this feature space. The resulting recordings become a set of matrices with fixed width equal to the number of features used, and varying length equal to the number of target movements in that recording. The transformer applies attention heads that are able to identify informative movements by looking at relationships with other movements. This allows the algorithm to find and model larger scale patterns than other algorithms. Aside from these heads, the rest of the algorithm may be either a multi-layer perceptron or a convolutional neural network.

The system may also utilize these statistical/machine learning techniques to determine a profile for abnormal eye movement that does not correlate with either impairment or normal sober eye movement. This abnormal eye movement may be a sign of impairment on an unknown substance or combination of substances, a sign of a head injury or other neurological abnormality, or another reason. Classification of a test subject's eye movement as abnormal, but not associated with known substances of impairment, and the communication of this to the test administrator, or other third party, may therefore be valuable information.

Other equipment that may be used in the process includes an optional external or adjunct device running a software application, which can be used by a test subject or administrator to communicate with the testing apparatus. This companion software application may be utilized by test administrators, or test subjects to enter additional information that the test apparatus cannot automatically detect. For example, demographic data, personally identifiable information, or other notes may be entered. This application can also be used to perform processing of the data from tests if required. Lastly, this application may be used to display results or other feedback on the test, such as upload status or other information.

This companion software application may include several key user interface functionalities, namely: a button used to start and/or stop the test, an indication of the test progress, and an indication of test results once the test data has been evaluated. Optional other functionality may include a live view from the cameras of the apparatus, a live animation of the view from the cameras, the ability to enter demographic data, display data upload status, the ability to enter individual identifiers like an employee ID number, the ability to watch recorded test video, the ability to enter suspected or known substances of impairment, and the ability to enter notes or testing rationale.

If a subject is found to be impaired or with abnormal eye movement due to one or multiple tests, the test results may be communicated automatically to the test administrator, or other third party as required. This is accomplished through any of the following methods: email, SMS/MMS messages, notification utilizing the companion software application, or any other digital means. The data may be utilized in evaluated form, or in raw form by test administrators, test subjects, or other interested parties as required.

If a subject is found to be not impaired, the test data may similarly be made available, or stored for later reference. Test subjects could alternatively request that test data be deleted rather than stored.

An output of the apparatus may be video recording and/or digital imagery which is not evaluated, used to train evaluative algorithms, or altered by the system. The video recording and/or imagery is captured by one or more cameras and stored either on the testing apparatus, on a mobile or desktop computing platform, or in cloud computing environments. This video and/or imagery can then be evaluated by existing human Drug Recognition Experts or other interested parties as required. Either visible or infrared cameras may be utilized to capture video and imagery from the automatically performed tests. The eye tracking video recording may be displayed in raw format, or optional test data such as gaze direction, pupil size, or stimulus may be overlayed on the video or displayed in conjunction with the video to provide additional important contextual information.

FIG. 1 is a flow chart of an embodiment of a method 100 to determine whether a test subject is unimpaired, impaired, and/or the substance that has impaired the test subject. The method 100 includes using a testing apparatus, at step 105. Optionally, the method 100 may include testing subject compliance monitoring, at step 110. For example, a user may not be in compliance by simply closing one or both of their eyes for some or all of the testing process. Additional types of non-compliance can include, but are not limited to, looking straight ahead or at another random point for the duration or part of the testing process, moving the eyes in a random manner for some or all of the testing process, tracking the stimulus only intermittently, ignoring test instructions, rapidly blinking for a sustained period of time, or cessation of stimulus tracking at any point. The detection of non-compliant users may be important step in accurately determining whether or not an individual is impaired.

The method 100 includes collecting data from the testing apparatus, at step 115. For example, that data collected may include, but is not limited to, eye movement video 120, pupil size data 125, gaze vector data 130, or the like. The data collected may include other data 135, such as other biometric data from a user. The method 100 includes storing data, at step 140. Optionally, the method 100 may include preprocessing the data, at step 145. The method 100 include processing the data with an automated impairment decision engine, at step 150.

The method 100 may include the automated impairment decision engine system using machine learning models, at step 155, to detect active (real-time) impairment from cannabis and other drugs, fatigue, or other conditions through the utilization of gaze vector data, pupil size data, and optionally other biometric data. The method 100 may include the automated impairment decision engine system using statistical models, at step 160, to detect active (real-time) impairment from cannabis and other drugs, fatigue, or other conditions through the utilization of gaze vector data, pupil size data, and optionally other biometric data. The method 100 includes matching a substance, at step 165. The matching of a substance may be based on machine learning models and/or statistical models. The method 100 includes reporting no impairment to the test administrator, at step 170. For example, if the automated impairment decision engine determines that a test subject is not impaired, the test administrator is informed of this decision. The method 100 includes reporting impairment and/or substance to the test administrator, at step 175. For example, if the automated impairment decision engine determines that a test subject is impaired, the test administrator is informed of this decision. Likewise, the automated impairment decision engine may inform the test administrator the substance which impaired the test subject.

Figure 2:
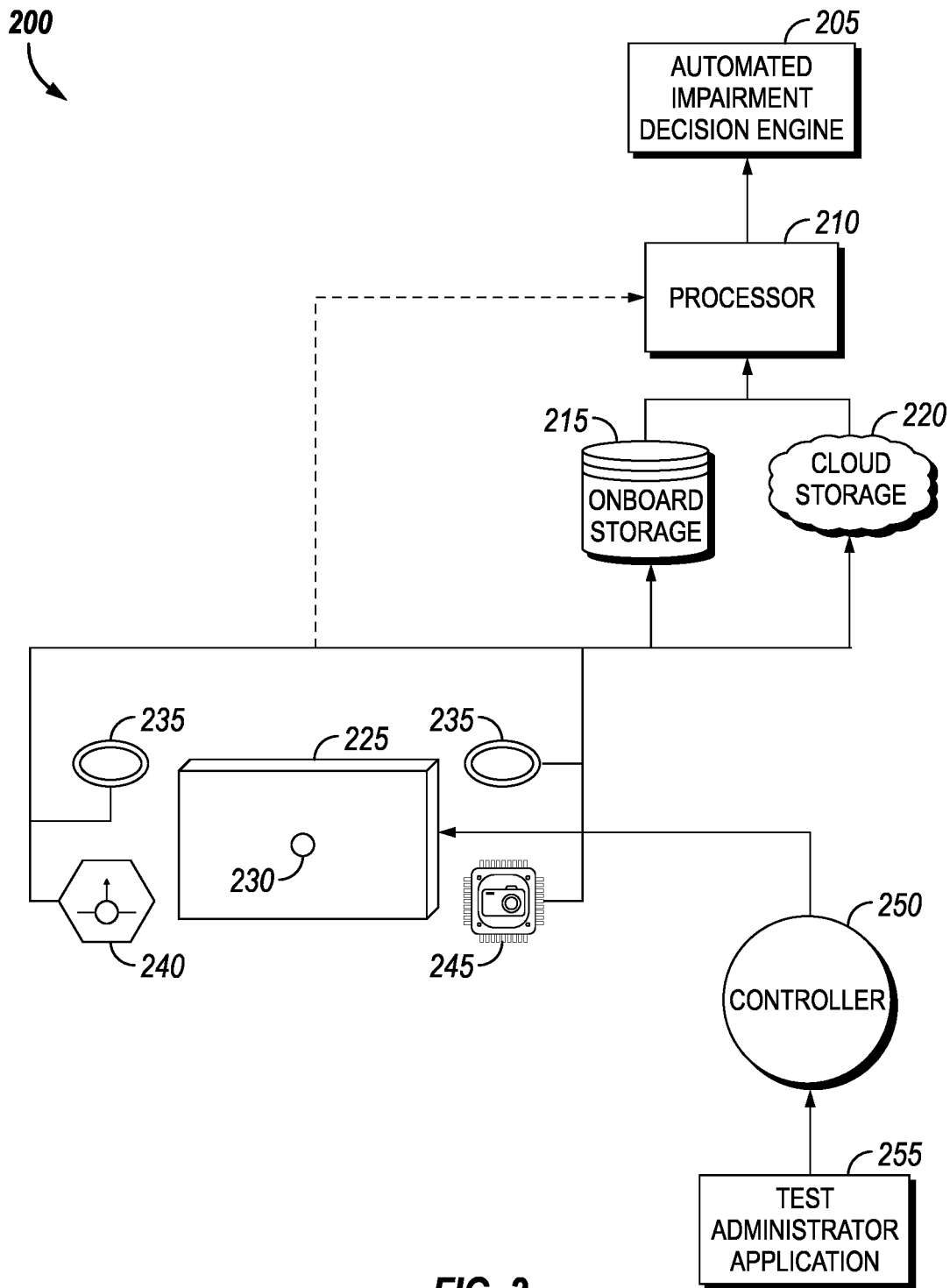
FIG. 2 shows a schematic of an embodiment of a system of the present disclosure.

FIG. 2 shows a schematic of an embodiment of a system 200 of the present disclosure. The system includes a test administrator application 255 connected, wired or wirelessly, to a controller 250. The controller 250 may be integral with the test administrator application 255 as would be appreciated by one of ordinary skill in the art having the benefit of this disclosure. The test administrator application 255 and controller 250 are connected to a display 225. The display 225 may be but is not limited to a monitor, video display, a virtual reality headset, television, monitor, kiosk-mounted display, augmented reality glasses, a holographic display, or the like. The connections of the system 200 may be wired or wireless as would be appreciated by one of ordinary skill in the art having the benefit this disclosure. The system 200 includes a stimulus 230 that is shown on the display 225. The stimulus 230 may be moved about the display 225 by the controller 250 and/or the test administrator application 255 as discussed herein.

The system 200 includes one or more eye tracking sensors 235. The one or more eye tracking sensors 235 monitor the eyes of a test subject during testing as discussed herein. The system 200 may include a camera 245. The camera 245 may be focused on the eye(s) of a test subject during testing. The system 200 may include one or more other sensors 240 as discussed herein. The data captured by the one or more eye tracking sensors 235, the camera 245, and/or the one or more other sensors 240 may be stored in onboard storage 215 and/or cloud storage 220 as would be appreciated by one of ordinary skill in the art having the benefit of this disclosure.

The system 200 includes a processor 210 and an automated impairment decision engine 205. The processor 210 may be integral to the automated impairment decision engine 205 as would be appreciated by one of ordinary skill in the art having the benefit of this disclosure. The processor 210 is configured to process the data from the one or more eye tracking sensors 235, the camera 245, and/or the one or more other sensors 240. The data may be received from the onboard storage 215 and/or the cloud storage 220. Alternatively, the data may be received directly from the one or more eye tracking sensors 235, the camera 245, and/or the one or more other sensors 240 as would be appreciated by one of ordinary skill in the art having the benefit of this disclosure. The automated impairment decision engine 205 uses the processed data to determine whether a test subject is impaired and/or the substance upon which a test subject is impaired as discussed herein.

Figure 3:
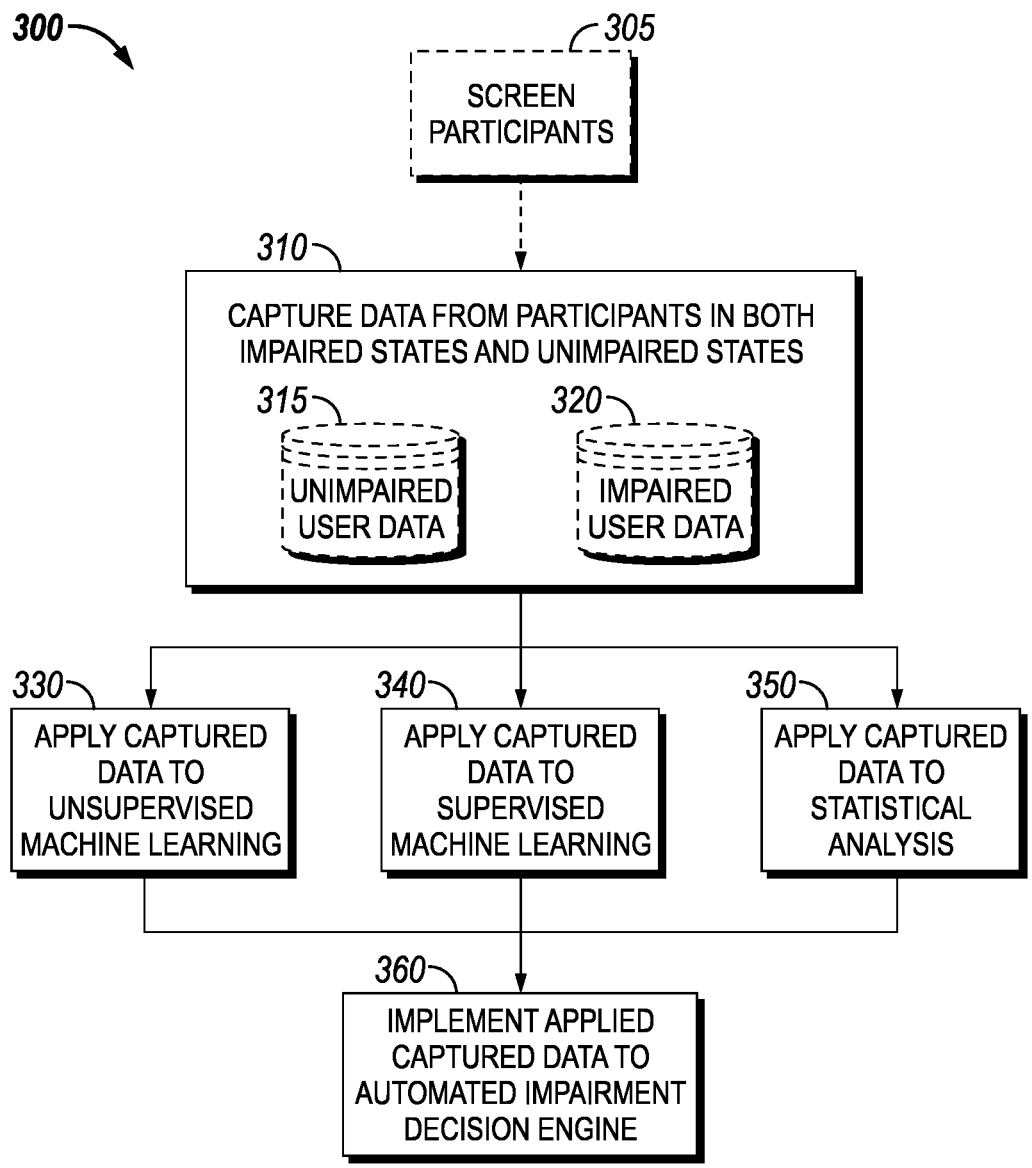
FIG. 3 is a flow chart of an embodiment of a method of the present disclosure.

FIG. 3 is a flow chart of an embodiment of a method of training a system or automated impairment decision engine to determine whether an individual is impaired or unimpaired. The method 300 includes capturing data from participants in both impaired states and unimpaired states, at step 310. The method 300 includes capturing both unimpaired user data 315 and impaired user data 320. Prior to capturing data, the method 300 may include screening participants, at step 305.

The method 300 includes applying captured data to unsupervised machine learning, at step 330. The method 300 includes applying captured data to supervised machine learning, at step 340. The method 300 includes applying captured data to statistical analysis, at step 350. The method 300 includes implementing applied captured data to an automated impairment decision engine, at step 360. One of ordinary skill in the art having the benefit of this disclosure would recognize that the applied captured data from unsupervised machine learning, the applied captured data from supervised machine learning, the applied captured data from statistical analysis, or the like may be used to train an automated impairment decision engine. Alternatively, applied captured data from all three or a combination may be used to train an automated impairment decision engine to determine whether a test subject is unimpaired, impaired, and/or the substance that has impaired the test subject as discussed herein.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives. Additionally, elements of a given embodiment should not be construed to be applicable to only that example embodiment and therefore elements of one example embodiment can be applicable to other embodiments. Additionally, in some embodiments, elements that are specifically shown in some embodiments can be explicitly absent from further embodiments. Accordingly, the recitation of an element being present in one example should be construed to support some embodiments where such an element is explicitly absent.

What is claimed is:

1. A system comprising:
a display;
a stimulus on the display;
a controller, wherein the controller is programmed to move the stimulus about the display;
one or more sensors, wherein the one or more sensors track eye movements and pupil size of a user due to movement of the stimulus or light conditions;
a dataset of impaired and sober individuals;
machine learning algorithms that are trained with the dataset of impaired and sober individuals;
a processor programmed to use the machine learning algorithms to analyze the eye movements and pupil size data;
a database of known test subjects;
wherein the processor is programmed to automatically identify the user based on eye measurement data if the user is contained within the database of known test subjects; and
wherein based on the automatic identification of the user the controller is programmed to administer certain tests that are most relevant to the user.

2. The system of claim 1, wherein the controller is programmed to move the stimulus to perform an impairment test and the processor is programmed to determine and evaluate impairment based on data from the one or more sensors.

3. The system of claim 1, wherein the controller is programmed to stimulate pupil response using varying light conditions to perform an impairment test and the processor is programmed to determine and evaluate impairment based on data from the one or more sensors.

4. The system of claim 1, wherein the one or more sensor capture pupil size data and wherein the processor is programmed to analyze the pupil size data to evaluate impairment.

5. The system of claim 1, wherein the one or more sensors capture gaze vector data of the user's vision and wherein the processor is programmed to analyze the captured gaze vector data to evaluate impairment.

6. The system of claim 5, wherein the display further comprises a virtual reality headset, television, monitor, kiosk-mounted display, augmented reality glasses, or a holographic display.

7. The system of claim 5, wherein the processor is programmed to utilize statistical models, machine learning, artificial intelligence algorithms, or a combination of these to analyze the eye movements or other biometric data.

8. The system of claim 7, wherein the controller is programmed to precisely calibrate the system to a face shape, eye characteristics, and eye geometry of the user.

9. The system of claim 8, wherein the controller is programmed to move the stimulus smoothly to the left and right or up and down.

10. The system of claim 9, wherein the controller is programmed to move the stimulus one or more times to a horizontal periphery of the user's vision.

11. The system of claim 10, wherein the controller is programmed to move the stimulus left or right and stop the movement at 45 degrees from center.

12. The system of claim 11, wherein the controller is programmed to move the stimulus to a vertical periphery of the user's vision.

13. The system of claim 12, wherein the controller is programmed to move the stimulus in a circle or to stimulate convergence in focus by bringing the stimulus toward the user's nose.

14. The system of claim 13, wherein the controller is programmed to display specific light levels and measure pupillary reflex response.

15. The system of claim 14, wherein the controller is programmed to capture data using skin-contact or non-contact sensors, the data includes temperature, heart rate, heart rate variability, respiratory rate, pulse oxygenation, heart rhythm, blood pressure, and muscle tone.

16. The system of claim 15, wherein the controller is programmed to perform chemical analysis on a sweat excreted by the user.

17. The system of claim 16, wherein the controller is programmed to measure lack of convergence, saccades, nystagmus, hippus, eye smoothness, reaction time, pupillary rebound dilation, and pupillary reflex for the purposes of impairment detection.

18. The system of claim 13, wherein the controller is programmed to group together data for the user.

19. The system of claim 13, wherein the controller is programmed to test for the ability for the user to hold the eyes in a converged position.

20. The system of claim 1, wherein the machine learning algorithms are trained to compensate for variability in capture rates of the one or more sensors.

21. The system of claim 1, further comprising an algorithm that finds a set of common features to describe eye movements of the user and transforms each into a feature space.

22. The system of claim 1, further comprising an algorithm to determine if a profile of eye movements of the user is abnormal and does not correlate with impairment or sober eye movement.

23. The system of claim 1, wherein the eye measurement data includes interpupillary distance, pupil size, or corneal print.

24. The system of claim 23, wherein the controller is programmed to administer certain tests that are most relevant to the user.

25. A system comprising:
a display;
a stimulus on the display;
a controller, wherein the controller is programmed to move the stimulus about the display;
one or more sensors, wherein the one or more sensors track eye movements and pupil size of a user due to movement of the stimulus or light conditions;
a dataset of impaired and sober individuals;
machine learning algorithms that are trained with the dataset of impaired and sober individuals;
a processor programmed to use the machine learning algorithms to analyze the eye movements and pupil size data;
an algorithm to determine if the user is following instructions during a testing process to determine if the user is being a non-compliant user; and
wherein the processor is programmed to notify a test administrator if the algorithm detects that the user is purposefully not following instructions during a testing process.

26. The system of claim 25, wherein the processer is programmed to notify a test administrator if the algorithm determines the user is being non-compliant.

27. A system comprising:
a display;
a stimulus on the display;
a controller, wherein the controller is programmed to move the stimulus about the display;
one or more sensors, wherein the one or more sensors track eye movements and pupil size of a user due to movement of the stimulus or light conditions;
a dataset of impaired and sober individuals;
machine learning algorithms that are trained with the dataset of impaired and sober individuals;
a processor programmed to use the machine learning algorithms to analyze the eye movements and pupil size data; and
a random number generator, wherein the random number generator determines a location of the stimulus on the display.

* * * * *